United States Patent [19]
Rech et al.

[11] Patent Number: 5,462,736
[45] Date of Patent: Oct. 31, 1995

[54] CRYSTAL CLEAR COSMETIC STICK COMPOSITION

[75] Inventors: Dawn M. Rech, Lake Hopatcong; Morton L. Barr, Rockaway, both of N.J.

[73] Assignee: The Mennen Company, Morristown, N.J.

[21] Appl. No.: 70,622

[22] Filed: Jun. 2, 1993

[51] Int. Cl.⁶ .................................................. A61K 7/32
[52] U.S. Cl. .................... 424/401; 424/DIG. 5; 424/65; 424/78.02; 514/715
[58] Field of Search ............... 424/401, 65, 78.02, 424/59, DIG. 5; 514/715

[56] References Cited

U.S. PATENT DOCUMENTS

| | | | |
|---|---|---|---|
| 2,890,987 | 6/1969 | Hilfer et al. | 424/DIG. 5 |
| 3,579,465 | 10/1967 | Schmolka | 252/316 |
| 4,165,293 | 8/1979 | Gordon | 252/118 |
| 4,252,789 | 2/1981 | Broad | 424/DIG. 5 |
| 4,268,498 | 5/1981 | Gedeon et al. | 424/DIG. 5 |
| 4,725,430 | 2/1988 | Schamper et al. | 424/DIG. 5 |
| 4,759,924 | 7/1988 | Luebbe et al. | 424/DIG. 5 |
| 4,772,424 | 9/1988 | Greeb | 252/546 |
| 4,816,261 | 3/1989 | Luebbe et al. | 424/DIG. 5 |
| 5,120,541 | 6/1992 | Macaulay et al. | 424/401 |
| 5,128,123 | 7/1992 | Brewster et al. | 424/401 |

FOREIGN PATENT DOCUMENTS

| | | |
|---|---|---|
| 0107330 | 9/1983 | European Pat. Off. . |
| 0450597 | 4/1991 | European Pat. Off. . |
| 0498488A2 | 1/1992 | European Pat. Off. . |

*Primary Examiner*—Raj Bawa
*Attorney, Agent, or Firm*—Antonelli, Terry, Stout & Kraus

[57] ABSTRACT

Disclosed is a clear, crystal-free, soap-gelled cosmetic stick composition. The composition includes a soap gelling agent (e.g., sodium stearate); at least two aliphatic polyhydric alcohols that are solvents for the soap gelling agent and that have a relatively small molecular weight and a relatively large molecular weight (e.g., propylene glycol and dipropylene glycol), respectively; a propoxylated ether that is a further solvent for the soap gelling agent, such as a propoxylated butyl ether (e.g., PPG-14 butyl ether); water; and a clarifying agent. The clarifying agent is a mixture of (a) a propoxylated fatty alcohol, such as a propoxylated myristyl ether (e.g., PPG-3 myristyl ether), and (b) a water-soluble, N-substituted aliphatic fatty acid amide surfactant (e.g., a combination of cocamide DEA and cocoyl sarcosine). The stick composition has improved surface aesthetics and improved payout, and has less pullaway from the container. The disclosed cosmetic stick composition can be a vehicle for various active materials, such as deodorant active materials, sunscreens, etc., so as to provide a clear deodorant stick, a sunscreen stick, etc.

48 Claims, No Drawings

CRYSTAL CLEAR COSMETIC STICK COMPOSITION

BACKGROUND OF THE INVENTION

The present invention relates to clear, crystal-free cosmetic stick compositions gelled by a soap (that is, a clear, crystal-free, soap-gelled cosmetic stick composition). Such clear, crystal-free cosmetic stick compositions can be a vehicle for incorporating, e.g., a deodorant active material, a sunscreen material, etc. therein so as to provide a clear deodorant stick composition (e.g., for axillary use), a sunscreen stick composition, etc. More particularly, the present invention is directed to clear deodorant stick compositions containing alcohol and water, and gelled with a soap gelling agent, and also containing deodorant active materials, which remain clear and crystal-free over extended periods of time.

It is desired to provide a clear, soap-gelled cosmetic stick composition (for example, a clear deodorant stick) having improved surface aesthetics and improved payout, with decreased shrinkage of the stick product (that is, which achieves less pullaway from the package when packaged in a stick dispensing container). Such clear cosmetic sticks have increased consumer appeal, and together with the other desired improved properties provides an improved product.

U.S. Pat. No. 4,268,498 to Gedeon, et al discloses substantially clear cosmetic sticks, having incorporated therein high levels of cosmetically active ingredients. The substantially clear cosmetic sticks contain, as essential ingredients, specific amounts of polyoxyethylene (17–23) -glucose-fatty acid ester; polyoxyethylene (20–26) ether of a long-chain alcohol; polyoxypropylene (2–5) ether of a long chain alcohol; sodium salt of a fatty acid; propylene glycol; lower alkyl ester of fatty acids; water; and cosmetically active ingredient. The long chain alcohols contain from 10 to 20 carbon atoms and include such alcohols as lauryl, myristyl, palmityl and the like, with a fatty acid moiety in the salts or esters containing from 12 to 20 carbon atoms and including such acids as dodecanoic, myristic, palmitic, oleic, stearic and the like. This patent is silent as to whether, and for how long, the clarity of the cosmetic stick is maintained, and does not describe any improvement in characteristics such as payout and shrinkage.

U.S. Pat. No. 4,759,924 to Luebbe, et al discloses transparent soap-gelled cosmetic stick compositions containing from about 40% to about 70% of a polyhydric aliphatic alcohol, from about 3% to about 10% of a soap; water; and from about 1% to about 20% of a hydro-alcoholic soluble emollient, the hydro-alcoholic soluble emollient having the following formula:

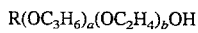

$$R(OC_3H_6)_a(OC_2H_4)_bOH$$

wherein R is either hydrogen or a hydrocarbon chain having from about 1 to 18 carbon atoms, preferably from about 4 to 16, and $a/(a+b) \leq 0.5$. Disclosed typical hydro-alcoholic soluble emollients include PPG-5-Ceteth 20, PPG-3-Myreth-3, PEG-20-Laurate, PEG-6-32 and Polyoxamer 335, these designations being designations of the Cosmetic, Toiletry and Fragrance Association (CTFA) as set forth in the *CTFA Cosmetic Ingredient Dictionary*, Second Edition (1977). This patent also discloses optional components that can be incorporated in the stick composition, including deodorant materials (i.e., deodorant active materials), perfumes, dyes, etc. The contents of U.S. Pat. No. 4,759,924 are incorporated herein by reference in their entirety.

European Patent Application (Published) No. 450597A2 (applicant: Bristol-Myers Squibb Co.) discloses transparent cosmetic gel stick compositions suitable for various cosmetic utilities, including that of a deodorant stick composition, comprising specific amounts of soap; water-soluble polyoxyalkylene ether of a fatty alcohol; polyoxyalkylene ether of a branched-chain fatty alcohol, having limited solubility in water; water; and aliphatic polyhydric alcohol having from 2 to 6 carbons and from 2 to 6 hydroxyl groups. This patent document discloses that the polyoxyalkylene ethers are functionally incorporated as emollients, and generally are polyoxyethylene ethers. This patent document further discloses that the clarity is improved by incorporating the polyoxyethylene ether of a branched-chain fatty alcohol (which is water-insoluble or water-dispersible) in the composition.

U.S. Pat. No. 5,120,541 to Macaulay, et al discloses a transparent cosmetic stick composition having a lamellar structure and including specific amounts of an alcohol (such as propylene glycol), a soap, and a soap crystal growth inhibitor. Examples of the soap crystal growth inhibitor include monoglycerides, diglycerides and triglycerides of specific fatty acids; salts of substituted fatty acids, the salts being formed by any suitable cation; salts of branched-chain fatty acids formed with any suitable cation; short-chain peptides; and other suitable materials including substituted or unsubstituted short-chain nonionics. This patent discloses that addition of the soap crystal growth inhibitor allows transparency to be attained even at levels of monohydric alcohol of up to 95% by weight; and that by selection of suitable packaging, it is possible to avoid the problem of shrinkage due to evaporation of alcohol.

U.S. Pat. No. 5,128,123 to Brewster, et al discloses clear cosmetic sticks containing specific amounts of a polyhydric alcohol having 2–6 carbon atoms and 2–6 hydroxyl groups, a soap and an alkoxylate copolymer, and further including a clarifying agent which is a basic amine present in an effective amount to maintain clarity of the stick. This patent discloses that the clarifying agent is preferably an amino alkanol having from 2 to 6 hydroxyl groups, these alkanols including anywhere from about 3 to about 18 carbon atoms and having molecular weights less than 1,000. This patent further discloses incorporation of various active materials in the stick compositions, to form deodorant sticks, sunscreen sticks, makeup sticks, etc. The contents of U.S. Pat. No. 5,128,123 are incorporated herein by reference in their entirety.

While the foregoing patent documents all disclose soap-gelled cosmetic sticks which are clear or transparent to some extent, it is still desired to provide cosmetic sticks that are clear and maintain such clarity over extended periods of time, thus having extended shelf life as a clear product, and moreover have improved surface aesthetics and improved payout, with less pullaway from the container (less shrinkage in the container, after being poured into the container as a liquid and then solidified).

U.S. Pat. No. 4,252,789 to Broad discloses soap-based deodorant sticks containing a mixture of sodium stearate and sodium palmitate in a specified weight ratio, and also containing specific amounts of a soap-compatible germicide, a compound selected from the group consisting of polyethylene imine and ethoxylated polyethylene imine, and water. This patent discloses that the added polyethylene imine or ethoxylated polyethylene imine causes the resulting stick to shrink slightly on setting up, rather than expanding as would occur without the added ingredient; and, moreover, temperature stability of the resulting stick is enhanced with the added ingredient. This patent does not disclose that the stick manufactured is clear.

U.S. Pat. No. 4,725,430 to Schamper, et al discloses a clear or translucent cosmetic stick containing, e.g., acidic antiperspirant-active salts and using dibenzyl monosorbitol acetal as the gelling agent. This patent discloses that when using the acidic antiperspirant-active salts, sodium stearate cannot be used as the gelling agent because the alkaline sodium stearate gelling agent would react with the salts.

U.S. Pat. No. 2,890,987 to Hilfer discloses astringent, antiperspirant and deodorant compositions in the form or shape of sticks, pencils, cylinders, and the like, the composition containing a water-insoluble metallic salt astringent, a normally solid higher fatty acid amide of an alkylolamine, a water-soluble alkylene polyhydric alcohol in which aqueous solutions of the astringent are soluble, and water.

Notwithstanding the foregoing, it is still desired to provide clear, crystal-free cosmetic stick compositions, which can be utilized (with active materials incorporated therein) as, e.g., a clear deodorant stick, a sunscreen stick, etc., and which maintain clarity over extended periods of time, avoiding crystal formation within the compositions; and, moreover, which have improved surface aesthetics and improved payout, and which have less pullaway from the container. It is particularly desired to provide such composition which can be used as a vehicle (e.g., solid stick base material) for deodorant actives such as Triclosan and/or deodorant perfume (fragrance), as well as for other active materials such as sunscreens.

SUMMARY OF THE INVENTION

Accordingly, it is an object of the present invention to provide a clear cosmetic stick composition that maintains its clarity over extended periods of time, without crystal formation in the composition (that is, a clear cosmetic stick that remains crystal-free).

It is a further object of the present invention to provide such clear cosmetic stick composition, having improved surface aesthetics and improved product payout, and less pullaway from the container.

It is a still further object of the present invention to provide a clear cosmetic stick that maintains its clarity over extended periods of time, and wherein a variety of active materials (for example, deodorant active materials, sunscreens, etc.) can be incorporated therein, while maintaining clarity.

It is a still further object of the present invention to provide a clear deodorant stick composition, having deodorant active materials (such as bacteriocides and fragrances) incorporated therein, that is clear and crystal-free, and maintains clarity over extended periods of time, without crystal formation in the stick, and which has improved surface aesthetics and improved product payout, with decreased shrinkage of the stick (less pullaway of the packaged product from the inside wall of the container).

The foregoing objectives are achieved according to the present invention by the presently-described clear cosmetic stick composition, which includes (a) a soap gelling agent; (b) at least two aliphatic polyhydric alcohols, which are solvents for the soap gelling agent and which have different molecular weights (a relatively small molecular weight and a relatively large molecular weight); (c) a propoxylated ether (propoxylated low molecular weight alcohol) which has low water solubility or is insoluble in water, and which is a further solvent for the soap gelling agent; (d) water; and (e) a clarifying agent, the clarifying agent including (i) a propoxylated ether (propoxylated fatty alcohol) and (ii) a water-soluble, N-substituted aliphatic fatty acid amide surfactant.

The soap gelling agent can be a salt of a fatty acid, and includes, illustratively and without limitation, sodium stearate. Illustratively and without limitation, the at least two aliphatic polyhydric alcohols can be propylene glycol and dipropylene glycol; however, the present invention is not limited thereto, and can include, for example, glycerine as a substitute for the propylene glycol, and can include dibutylene glycol rather than dipropylene glycol. In addition to the foregoing, and without limitation, various polyhydric alcohols which can be used in the present invention include any butylene glycol, e.g., 1,3-butylene glycol, dibutylene glycol, erythritol, pentaerythritol, diethylene glycol, triethylene glycol, ethyl hexanediols, glycerine, sorbitol, mannitol, any hexylene glycol, any hexanetriol, etc. As a guideline, polyhydric alcohols with up to 16 carbon atoms can be used.

The propoxylated ether (also called propoxylated low molecular weight alcohol) that is a further solvent for the soap gelling agent is, illustratively, a propoxylated butyl ether, e.g., PPG-14 butyl ether. This designation, PPG-14 butyl ether, is the designation of the Cosmetic, Toiletry and Fragrance Association (CTFA) in the *CTFA International Cosmetic Ingredient Dictionary* (4th Ed. 1991), the contents of which are incorporated herein by reference in their entirety. Throughout this specification, components of the described compositions are designated by their CTFA names. Other similar propoxylated ethers, that are solvents for the soap gelling agent and have a low water solubility, or are water-insoluble, can also be used; these include, for example, PPG-4-hexyl ether and PPG-10 butyl ether.

The composition according to the present invention has a solvent system, which solubilizes the soap gelling agent and (if present) the fragrance, that includes four components; the two polyhydric alcohols, the propoxylated ether (propoxylated low molecular weight alcohol) and water. It is a key to the present invention that the soap gelling agent and (if present) the fragrance be solubilized in the composition, to achieve a clear stick composition. While not being held to any theory, it is possible that the role of each of the solvent components is as follows. The lower molecular weight polyhydric alcohol is completely water soluble (soluble in all proportions with water). The propoxylated ether is water-insoluble or has very low water solubility. The combination of higher molecular weight and lower molecular weight polyhydric alcohols efficiently allows the propoxylated ether to become miscible with (or soluble in) water, to ensure both clarity and efficient solubilization of the soap gelling agent and the fragrance (if present).

The propoxylated ether that forms part of the clarifying agent can be, illustratively, a propoxylated myristyl ether, e.g., PPG-3 myristyl ether. Other propoxylated ethers that can be used as part of the clarifying agent include, for example, PPG-3 stearyl ether and PPG-2 cetyl ether.

Illustratively, and preferably, the water-soluble, N-substituted aliphatic fatty acid amide surfactant is a mixture of the following two types of compounds:

where RCO- is a fatty acid residue and R has a carbon chain length of $C_6$–$C_{22}$, one or both of X and Y is $(CH_2CH_2OH)$, and the other of X and Y can be hydrogen where only one of X and Y is $(CH_2CH_2OH)$; and

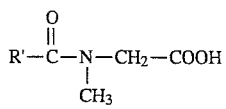

where R'CO- is a fatty acid residue and R' has a carbon chain length of $C_6$–$C_{22}$.

Optionally, the stick composition according to the present invention can also include a neutralizing agent; and illustratively (but not limiting) the neutralizing agent can be triethanolamine. Other neutralizing agents include, for example, sodium hydroxide, potassium hydroxide, aliphatic primary and secondary amines, sodium carbonate, polyethyleneimine, magnesium oxide, magnesium hydroxide, etc.

The composition according to the present invention can include various adjuvents, including dyes. Other adjuvents such as fragrances, bacteriocides, sunscreens, etc. can be incorporated in the stick composition, depending upon the ultimate end use. Thus, the cosmetic stick composition according to the present invention can be used as a vehicle for various active materials, depending upon the ultimate end use of the product. See, e.g., U.S. Pat. No. 4,759,924, and U.S. Pat. No. 5,128,123, the contents of each of which have been incorporated herein by reference in their entirety, for various adjuvents that can be incorporated in the cosmetic stick composition of the present invention.

Adjuvents which may optionally be included in the composition according to the present invention also include emollients such as fatty esters, fatty ethers and fatty alcohols, alkyl polyglucosides, glyceryl esters of fatty acids, oils such as mineral oils or silicone (such as cyclomethicone or dimethicone), diesters of adipic, succinic or other similar carboxylic acids, propoxylated/ethoxylated fatty alcohols such as PPG-3-Myreth-3, natural extracts such as lichen, cucumber, coriander, carob, carrot, aloe and the like, and additional clarifying agents such as low levels of stearyl alcohol and salt (e.g., sodium chloride).

Accordingly, through the present invention a clear cosmetic stick composition is achieved that maintains clarity over extended periods of time, while remaining substantially crystal free; and which has improved surface aesthetics and improved product payout; while also reducing pullaway from the dispensing container in which the composition is packaged for sale to the consumer (a melt of the composition having been cast into the dispensing container).

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, where compositions are described as including or comprising specific components, it is contemplated that compositions of the present invention also consist essentially of, or consist of, the recited components. Accordingly, throughout the present disclosure any described composition can consist essentially of, or consist of, the recited components.

Throughout the present disclosure, by water soluble is meant substantially complete solubility, in substantially all proportions, of water and the other material. By water insoluble, it is meant that substantially no amount of the material is soluble in water, and vice-versa. Low water solubility means that only a small amount of the material (e.g., at most 5% by weight, of the weight of the water) is soluble in the water.

Throughout the present disclosure, by a "clear" composition is meant a composition which is visually clear, with a minimal amount of haziness or cloudiness. The composition, packaged in a transparent container, allows ready viewing of objects behind it, similar to properties of glass. By contrast, a product that is insufficiently clear causes light passing through it to be scattered, making it difficult to clearly see objects behind it. The clear composition of around 1 inch in thickness allows at least 60% of incident light at 700 nm to pass through it, using a standard UV-Visible spectrophotometer with appropriate attachments to allow the composition (e.g., in a clear package) to be evaluated for light transmission. After 5 freeze-thaw cycles (cycling the composition in a clear package five times from room temperature to below 32° F. so as to allow the composition to freeze), the light transmission as described above is to be at least 50%.

The present invention provides a clear cosmetic stick composition, that can be used as a vehicle for active materials such as deodorant active and sunscreen active materials, which composition is substantially crystal-free, and maintains clarity over extended periods of time and remains substantially crystal-free, and which has improved surface aesthetics and product payout, while having less pullaway from the dispensing container. The composition is galled with a soap gelling agent, and includes, in addition to the soap gelling agent, at least two aliphatic polyhydric alcohols, which are solvents for the soap gelling agent and which have different molecular weights; a propoxylated ether (propoxylated low molecular weight alcohol) that is a further solvent for the soap gelling agent, which propoxylated ether has a low water solubility or is water-insoluble; water; and a clarifying agent, the clarifying agent including (i) a propoxylated ether (propoxylated fatty alcohol) and (ii) a water-soluble, N-substituted aliphatic fatty acid amide surfactant.

As mentioned previously, a first component of the present clear cosmetic stick composition is a soap gelling agent (that is, a soap as a gel forming agent). Desirably, the soap gelling agents are sodium, potassium and triethanolamine salts of fatty acids containing from about 12 to 22 carbon atoms, as known in the art. See U.S. Pat. No. 5,128,123, the contents of which have previously been incorporated herein by reference. The soap gelling agent is, illustratively, included in the clear stick composition in an amount of about 5–8% by weight, of the total weight of the composition. A particularly preferred soap gelling agent is sodium stearate. Mixtures of different soaps can be utilized, including soaps having the same cation (e.g., sodium) but whose fatty acids contain different lengths of carbon atoms, and soaps having the same fatty acid component (e.g., stearate) but whose cations differ (e.g., sodium, potassium, triethanolamine).

The present clear cosmetic stick composition includes at least two aliphatic polyhydric alcohols, which are solvents for the soap gelling agent and which have different molecular weights (e.g., one aliphatic polyhydric alcohol having a relatively small molecular weight and a second aliphatic polyhydric alcohol having a relatively large molecular weight, the molecular weights being small and large relative to each other). An illustrative combination of polyhydric alcohols includes propylene glycol and dipropylene glycol; also illustratively (and not limiting), glycerine can be substituted for the propylene glycol and dibutylene glycol can be substituted for the dipropylene glycol. While not limiting of the present invention, polyhydric aliphatic alcohols containing 2–16 carbon atoms, and from 2 to 16 hydroxyl groups, can be utilized in the present invention, as long as they meet the requirements set out in the foregoing. The stick composition preferably includes 30–60% by weight, of the total weight of the composition, of the aliphatic polyhydric alcohols. A range for the weight ratio of low molecular weight polyhydric alcohol to high molecular weight polyhydric alcohol ($L_{MW}/H_{MW}$), in the composition, is, illustratively (and not limiting), 6.0 to 0.30, preferably 3.0 to 0.80.

The composition according to the present invention also includes a propoxylated ether as a further solvent for the soap gelling agents; this propoxylated ether has a low water solubility, or is water-insoluble. An appropriate propoxylated ether for this component of the clear cosmetic stick composition of the present invention is a propoxylated butyl ether, such as PPG-14 butyl ether, although such material is not limiting. The propoxylated ether that is a solvent for the soap gelling agent is preferably incorporated in a composition in the amount of 10–30% by weight, of the total weight of the composition.

Generally, the propoxylated ether that is a further solvent for the soap gelling agent can be represented by the general formula:

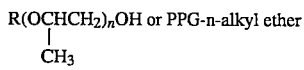

where R (alkyl) is straight chain or branched, and R (alkyl) contains 4–9, preferably 4, carbon atoms, and where n varies from 2 to 20, preferably 6–16. Thus, this propoxylated ether can be branched or straight chain.

The composition according to the present invention also includes water (e.g., deionized water), for example, in an amount of 2–30% by weight, preferably of 10–20% by weight, of the total weight of the composition.

As mentioned previously, the composition according to the present invention also includes a clarifying agent. This clarifying agent includes, for example, a propoxylated ether and a water-soluble, N-substituted aliphatic fatty acid amide surfactant.

The propoxylated ether (propoxylated fatty alcohol) which forms part of the clarifying agent is preferably a propoxylated myristyl ether; and, illustratively, is PPG-3 myristyl ether. This propoxylated ether that forms part of the clarifying agent is incorporated in the composition preferably in an amount of 1–10%, more preferably 3–5%, by weight, of the total weight of the composition.

Generally, the propoxylated ether which forms part of the clarifying agent can be represented by the general formula:

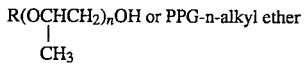

where R (or alkyl) is a straight chain or branched chain aliphatic fatty group from 10 to 22 carbon atoms, preferably, 14–16 carbon atoms, and where n varies from 1 to 5, preferably n=3. Thus, this propoxylated ether can be branched or straight-chain.

The water-soluble, N-substituted aliphatic fatty acid amide surfactant which forms part of the clarifying agent is desirably a mixture of the following components:

where RCO- is a fatty acid residue and R has a carbon chain length of $C_6$–$C_{22}$, and one or both of X and Y is ($CH_2CH_2OH$), with the other of X and Y being H when only one of X and Y is ($CH_2CH_2OH$); and

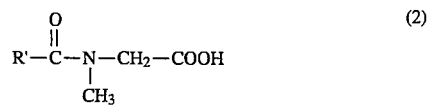

where R'CO- is a fatty acid residue and R' has a carbon chain length of from $C_6$–$C_{22}$. Preferably, the carbon chain length for each of the two foregoing components of the water-soluble, N-substituted aliphatic fatty acid amide surfactant is $C_{12}$–$C_{18}$; at a carbon chain length of as low as 6 carbon atoms, the efficiency of the surfactants as clarifying agents is not as great as at the higher carbon chain lengths.

Note that the foregoing component (2) contains a carboxylic acid moiety, which is not anionic. However, at the pH in the clear cosmetic composition (e.g., pH of the soap), the carboxylic acid group is ionized and is therefore anionic. Thus, in this component (2) the carboxylic acid moiety may or may not be ionized.

A specific, preferred water-soluble, N-substituted aliphatic fatty acid amide surfactant is a mixture of cocamide DEA and cocoyl sarcosine (as named in the *CTFA International Cosmetic Ingredient Dictionary* (4th Ed. 1991)). The mixture of cocamide DEA and cocoyl sarcosine is sold as a mixture of the two ingredients by Croda, Inc., under the name "INCROMIDE CAC". The cocamide DEA and cocoyl sarcosine respectively have the following structures:

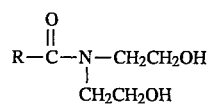

Cocamide DEA, where R are fatty groups from coconut oil (DEA=diethanolamine); and

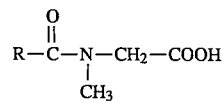

Cocoyl Sarcosine, where R are fatty groups from coconut oil.

The "INCROMIDE CAC" is a clear viscous liquid having a color (Gardner) of 4 Max, having a bland odor, and a pH (3% aqueous solution) of 8.6–9.2. Moreover, the "INCROMIDE CAC" has a base value of 100–110.

In the "INCROMIDE CAC" which has a pH of 8.6–9.2, the carboxylic acid moiety of the cocoyl sarcosine is ionized.

The two components of the water-soluble, N-substituted aliphatic fatty acid amide surfactant (that is, the mono- or di-ethanolamine and the sarcosine compounds) are desirably included in a weight ratio to each other of 80:20 to 20:80. The water-soluble, N-substituted aliphatic fatty acid amide surfactant is included in the composition in an amount of 2–8% by weight, preferably 4–6% by weight, of the total weight of the composition.

The composition optionally includes a neutralizing agent, in an amount up to and including 3% by weight, of the total weight of the composition. An illustrative neutralizing agent is triethanolamine, although the neutralizing agents are not limited to this specific neutralizing agent, as described previously.

As indicated previously, depending on the desired end use and desired appeal to consumers, the composition can include various adjuvents, e.g., fragrances, bacteriocides (such as Triclosan), dyes, sunscreens, etc. Of course, the adjuvents added are to be compatible with the above-described components; and, in particular, should not interfere with the formation of the gel (solid stick) by the soap gelling agent. These adjuvents can include, besides previously mentioned fragrances, bacteriocides and sunscreens, skin conditioners, nail conditioners and the like.

In particular, cosmetically active ingredients which dissolve to yield a clear composition are desirable for use in the compositions of the present invention.

Where the composition is to be utilized as a deodorant, preferably the composition includes a fragrance and a bacteriocide. The fragrance illustratively is included in the composition in an amount of 1.0% by weight, of the total weight of the composition; and the bacteriocide illustratively is included in the composition in an amount of 0.25% by weight, of the total weight of the composition.

Furthermore, preservatives may also be added. Other various optional components which may be included are described in U.S. Pat. No. 4,759,924 and U.S. Pat. No. 5,128,123, the contents of each of which have previously been incorporated herein by reference in their entirety.

The gel sticks of the present invention are made by combining the ingredients in liquid form; generally, heat must be applied in order to provide the ingredients in liquid (melted) form. More volatile components of the composition (e.g., fragrances) should be added near the end of the mixing cycle, and preferably at lower temperatures (while still maintaining the mixture as a liquid), to avoid volatilization of the more volatile components from the mixture. After combining the ingredients, the mixture is poured into a form having the desired shape (e.g., a stick deodorant package (dispensing container)). The poured mixture is cooled, so as to solidify.

As one embodiment of the present invention having consumer appeal, the package for the stick product (e.g., deodorant stick product) is clear. Pullaway (including excessive localized shrinkage) from the package (container) is particularly disadvantageous when the product is packaged in a clear container, since such pullaway reduces the aesthetics of a clear product by producing blemishes easily visible to the consumer. The present composition has particular advantages in a clear package, because it has less pullaway from the package (container), and thus provides a clearer final product, with less blemishes, in the clear package.

The cosmetic stick composition according to the present invention, after being formed into packaged sticks, is used by the consumer by rubbing the stick on, e.g., the area of the body where application is desired, depositing active materials on the skin surface. Thus, the compositions according to the present invention are utilized by conventional techniques. For example, when utilizing compositions according to the present invention as a deodorant solid stick, having deodorant active materials incorporated therein, the solid stick product is elevated out of the dispensing package so as to expose the stick, and the exposed portion of the stick is then rubbed against, e.g., the axillary region of the human body so as to deposit the deodorant active materials in the axillary region.

The following examples further describe and demonstrate embodiments within the scope of the present invention. The examples are given solely for the purpose of illustration and are not to be construed as limitations of the invention. Many variations thereof are possible without departing from the spirit and scope of the present invention.

In the following examples, the concentration (%) is in percent by weight, of the total weight of the composition.

| Constituent | Concentration (%) |
|---|---|
| EXAMPLE 1 | |
| Propylene Glycol | 36.75 |
| Dipropylene Glycol | 15.0 |
| PPG-14 Butyl Ether | 15.0 |
| INCROMIDE CAC | 6.0 |
| PPG-3 Myristyl Ether | 3.0 |
| Triclosan | 0.25 |
| Sodium Stearate | 6.5 |
| Triethanolamine | 1.5 |
| Deionized Water | 15.0 |
| Fragrance | 1.0 |
| EXAMPLE 2 | |
| Propylene Glycol | 23.75 |
| Dipropylene Glycol | 23.75 |
| PPG-14 Butyl Ether | 23.75 |
| INCROMIDE CAC | 6.0 |
| PPG-3 Myristyl Ether | 5.0 |
| Triclosan | 0.25 |
| Sodium Stearate | 6.5 |
| Deionized Water | 10.0 |
| Fragrance | 1.0 |
| EXAMPLE 3 | |
| Propylene Glycol | 43.25 |
| Dipropylene Glycol | 15.0 |
| PPG-14 Butyl Ether | 15.0 |
| INCROMIDE CAC | 6.0 |
| PPG-3 Myristyl Ether | 3.0 |
| Triclosan | 0.25 |
| Sodium Stearate | 6.5 |
| Deionized Water | 10.0 |
| Fragrance | 1.0 |

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A clear cosmetic stick composition comprising:

(a) a soap gelling agent;

(b) at least two aliphatic polyhydric alcohols, which are solvents for the soap gelling agent, wherein the at least two aliphatic polyhydric alcohols include a first aliphatic polyhydric alcohol and a second aliphatic polyhydric alcohol, the first aliphatic polyhydric alcohol having a first molecular weight and the second aliphatic polyhydric alcohol having a second molecular weight, the first molecular weight always being larger than the second molecular weight;

(c) a propoxylated ether that is a further solvent for the soap gelling agent, the propoxylated ether being PPG-n alkyl ether, where the alkyl group is straight chain or branched and has 4–9 carbon atoms, and where n is 2–20, the propoxylated ether having a solubility in water of at most 5% by weight, of the weight of water for dissolving the propoxylated ether;

(d) water, in an amount of 2–30% by weight, of the total weight of the composition; and (e) a clarifying agent, the clarifying agent including (i) a propoxylated fatty alcohol, and (ii) a water-soluble, N-substituted aliphatic fatty acid amide surfactant, the water-soluble, N-substituted aliphatic fatty acid amide surfactant being included in an amount of 2–8% by weight, of the total weight of the composition.

2. A clear cosmetic stick composition according to claim 1, wherein said soap gelling agent includes a salt of a fatty acid.

3. A clear cosmetic stick composition according to claim 2, wherein said salt of a fatty acid includes sodium stearate.

4. A clear cosmetic stick composition according to claim 2, wherein the composition includes, in percent by weight of the total weight of the composition, 5–8% by weight soap gelling agent, 30–60% by weight at least two aliphatic polyhydric alcohols, 10–30% by weight propoxylated ether that is a further solvent for the soap gelling agent, and 1–10% by weight propoxylated fatty alcohol.

5. A clear cosmetic stick composition according to claim 4, wherein said water-soluble, N-substituted fatty acid amide surfactant is a mixture of:

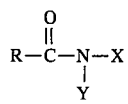
(A)

where RCO- is a fatty acid residue and R has a carbon chain length of $C_6$–$C_{22}$, and at least one of X and Y is ($CH_2CH_2OH$), with the other of X and Y being H where only one of X and Y is ($CH_2CH_2OH$); and

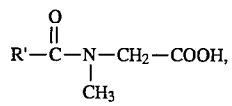
(B)

where R'CO- is a fatty acid residue and R' has a carbon chain length of $C_6$–$C_{22}$.

6. A clear cosmetic stick composition according to claim 5, wherein each of R and R' has a carbon chain length of $C_{12}$–$C_{18}$.

7. A clear cosmetic stick composition according to claim 5, wherein a weight ratio of (A) to (B), in said water-soluble, N-substituted fatty acid amide surfactant, is 20:80 to 80:20.

8. A clear cosmetic stick composition according to claim 7, wherein said water-soluble, N-substituted aliphatic fatty acid amide surfactant is a mixture of cocamide DEA and cocoyl sarcosine.

9. A clear cosmetic stick composition according to claim 5, wherein said water-soluble, N-substituted aliphatic fatty acid amide surfactant is a mixture of cocamide DEA and cocoyl sarcosine.

10. A clear cosmetic stick composition according to claim 9, wherein said at least two polyhydric alcohols include propylene glycol and dipropylene glycol respectively as the second and first aliphatic polyhydric alcohols.

11. A clear cosmetic stick composition according to claim 10, wherein said propoxylated ether that is a further solvent for the soap gelling agent is PPG-14 butyl ether.

12. A clear cosmetic stick composition according to claim 11, wherein said propoxylated fatty alcohol forming part of the clarifying agent is PPG-3 myristyl ether.

13. A clear cosmetic stick composition according to claim 12, wherein the composition further includes a neutralizing agent, included in the composition in an amount up to and including 3% by weight of the total weight of the composition.

14. A clear cosmetic stick composition according to claim 13, wherein said neutralizing agent is triethanolamine.

15. A clear cosmetic stick composition according to claim 12, wherein the composition further includes a deodorant active material.

16. A clear cosmetic stick composition according to claim 15, wherein said deodorant active material includes fragrances and bacteriocides.

17. A clear cosmetic stick composition according to claim 1, wherein said water-soluble, N-substituted aliphatic fatty acid amide surfactant is a mixture of:

(A)

where RCO- is a fatty acid residue and where R has a carbon chain length of $C_6$–$C_{22}$, and at least one X and Y is ($CH_2CH_2OH$), with the other of X and Y being H when only one of X and Y is ($CH_2CH_2OH$); and

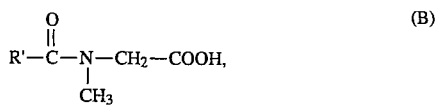
(B)

where R'CO- is a fatty acid residue and R' has a carbon chain length of $C_6$–$C_{22}$.

18. A clear cosmetic stick composition according to claim 17, wherein said at least two aliphatic polyhydric alcohols include propylene glycol and dipropylene glycol respectively as the second and first aliphatic polyhydric alcohols, wherein said propoxylated ether that is a further solvent for the soap gelling agent is PPG-14 butyl ether, and wherein said propoxylated fatty alcohol forming part of the clarifying agent is PPG-3 myristyl ether.

19. A clear cosmetic stick composition according to claim 18, wherein said soap gelling agent includes sodium stearate.

20. A clear cosmetic stick composition according to claim 19, wherein the composition further includes a deodorant active material.

21. A clear cosmetic stick composition according to claim 1, wherein said propoxylated ether that is a further solvent for the soap gelling agent is a propoxylated butyl ether, and the propoxylated fatty alcohol that forms part of the clarifying agent is a propoxylated myristyl ether.

22. A clear cosmetic stick composition according to claim 21, wherein said soap gelling agent includes a salt of a fatty acid.

23. A clear cosmetic stick composition according to claim 22, wherein said water-soluble, N-substituted aliphatic fatty acid amide surfactant is a mixture of:

(A)

where RCO- is a fatty acid residue and R has a carbon chain length of $C_6$–$C_{22}$, and at least one of X and Y is ($CH_2CH_2OH$), with the other of X and Y being H where only one of X and Y is ($CH_2CH_2OH$); and

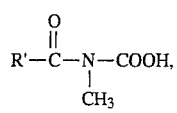

where R'CO- is a fatty acid residue and R' has a carbon chain length of $C_6$–$C_{22}$.

24. A clear cosmetic stick composition according to claim 23, wherein a weight ratio of (A) to (B), in said water-soluble, N-substituted aliphatic fatty acid amide surfactant, is 20:80 to 80:20.

25. A clear cosmetic stick composition according to claim 24, wherein the composition includes, in percent by weight of the total weight of the composition, 5–8% by weight soap gelling agent, 30–60% by weight at least two aliphatic polyhydric alcohols, 10–30% by weight propoxylated butyl ether, water, and 1–10% by weight propoxylated myristyl ether.

26. A clear cosmetic stick composition according to claim 1, wherein the propoxylated fatty alcohol is PPG-n-alkyl ether, where the alkyl group is straight chain or branched and contains 10–22 carbon atoms, and where n is 1–5.

27. A clear cosmetic stick composition according to claim 26, wherein said water-soluble, N-substituted aliphatic fatty acid surfactant is a mixture of:

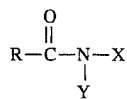

where RCO- is a fatty acid residue and R has a carbon chain length of $C_6$–$C_{22}$, and at least one of X and Y is ($CH_2CH_2OH$), with the other of X and Y being H where only one of X and Y is ($CH_2CH_2OH$); and

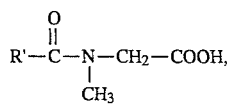

where R'CO- is a fatty acid residue and R' has a carbon chain length of $C_6$–$C_{22}$.

28. A clear cosmetic stick composition according to claim 27, wherein a weight ratio of (A) to (B), in said water-soluble, N-substituted aliphatic fatty acid amide surfactant, is 20:80 to 80:20.

29. A clear cosmetic stick composition according to claim 28, wherein the at least two aliphatic polyhydric alcohols are each aliphatic polyhydric alcohols containing 2–16 carbon atoms and 2–16 hydroxyl groups.

30. A clear cosmetic stick composition according to claim 29, wherein a weight ratio of first aliphatic polyhydric alcohol to high molecular weight aliphatic polyhydric alcohol is in a range of 6.0 to 0.30.

31. A clear cosmetic stick composition according to claim 30, wherein said soap gelling agent includes a salt of a fatty acid.

32. A clear cosmetic stick composition according to claim 31, wherein the composition includes, in percent by weight of the total weight of the composition, 5–8% by weight soap gelling agent, 30–60% by weight at least two aliphatic polyhydric alcohols, 10–30% by weight propoxylated ether that is a further solvent for the soap gelling agent, and 1–10% by weight propoxylated fatty alcohol.

33. A clear cosmetic stick composition according to claim 32, wherein the composition further includes a deodorant active material.

34. A clear deodorant stick composition according to claim 33, packaged in a clear container.

35. A clear cosmetic stick composition according to claim 32, packaged in a clear container.

36. A clear cosmetic stick composition according to claim 1, packaged in a clear container.

37. A clear cosmetic stick composition according to claim 1, wherein said propoxylated ether that is a further solvent for the soap gelling agent is selected from the group consisting of PPG-14 butyl ether, PPG-4 hexyl ether and PPG-10 butyl ether.

38. A clear cosmetic stick composition according to claim 1, wherein the alkyl group of the PPG-n alkyl ether has 4 carbon atoms.

39. A clear cosmetic stick composition according to claim 1, wherein water is included in the composition in an amount of 10%–20% by weight, of the total weight of the composition.

40. A clear cosmetic stick composition according to claim 1, wherein the water-soluble, N-substituted aliphatic fatty acid amide surfactant is a mixture of cocamide DEA and cocoyl sarcosine.

41. A clear cosmetic stick composition according to claim 40, wherein cocamide DEA and cocoyl sarcosine are included in the composition in a weight ratio to each other in the range of 80:20 to 20:80.

42. A clear cosmetic stick composition according to claim 20, wherein the deodorant active material includes a fragrance.

43. A clear cosmetic stick composition comprising:
   (a) sodium stearate as a soap gelling agent;
   (b) a mixture of propylene glycol and dipropylene glycol;
   (c) PPG-14 butyl ether;
   (d) water, in an amount of 2–30% by weight, of the total weight of the composition;
   (e) PPG-3 myristyl ether; and
   (f) a mixture of cocamide DEA and cocoyl sarcosine, said mixture being included in the composition in an amount of 2–8% by weight, of the total weight of the composition.

44. A clear cosmetic stick composition according to claim 43, wherein the composition includes, in percent by weight of the total weight of the composition, 5–8% by weight soap gelling agent, 30–60% by weight of the mixture of propylene glycol and dipropylene glycol, 10–30% by weight PPG-14 butyl ether, and 1–10% by weight PPG-3 myristyl ether.

45. A clear cosmetic stick composition according to claim 44, wherein water is included in the composition in an amount of 10–20% by weight, of the total weight of the composition.

46. A clear cosmetic stick composition according to claim 45, wherein the dipropylene glycol and propylene glycol are included in a weight ratio of dipropylene glycol:propylene glycol of 6.0:1 to 0.30:1; and the cocamide DEA and cocoyl sarcosine are included in a weight ratio of cocamide DEA-:cocoyl sarcosine of 80:20 to 20:80.

47. A clear cosmetic stick composition according to claim 15, wherein the deodorant active material is dissolved in the composition.

48. A clear cosmetic stick composition according to claim 47, wherein the deodorant active material is a fragrance, dissolved in the composition.

* * * * *